United States Patent [19]

Hodge

[11] 4,018,916

[45] Apr. 19, 1977

[54] ANTIVIRAL IONIC COMPLEXES OF DOUBLE-STANDARD RNA

[75] Inventor: Richard Anthony Vere Hodge, Dorking, England

[73] Assignee: Beecham Group Limited, United Kingdom

[22] Filed: June 25, 1975

[21] Appl. No.: 590,033

Related U.S. Application Data

[62] Division of Ser. No. 544,211, Jan. 12, 1975.

[52] U.S. Cl. .............................. 424/180; 536/27; 536/28; 536/29

[51] Int. Cl.$^2$ ...................................... A61K 31/70

[58] Field of Search .............. 260/211.5 R; 424/180

[56] References Cited

UNITED STATES PATENTS 3,775,398  11/1973  Harnden .................... 260/211.5 R
3,845,033  10/1974  Harnden .................... 260/211.5 R

*Primary Examiner*—Johnnie R. Brown

[57] ABSTRACT

Ionic complexes of double-stranded ribonucleic acids in which the cations are ammonium polymer polycations, demonstrate antiviral activity.

8 Claims, No Drawings

ANTIVIRAL IONIC COMPLEXES OF DOUBLE-STANDARD RNA

This is a division of Ser. No. 544,211 filed Jan. 12, 1975.

This invention relates to antiviral substances, to a method for their preparation, and to pharmaceutical (including veterinary) compositions comprising them.

It is now generally recognized that double-stranded ribonucleic acids are potent inducers of interferons and thus should be of value in the broad spectrum prophylaxis of viral infections, and, to a lesser extent, in the treatment of such infections. Double-stranded ribonucleic acids of both natural and synthetic origin have been shown to possess interferon — inducing and antiviral activity in tissue culture and in whole animals. Among the specific sources of interferon — inducing double-stranded ribonucleic acid which have been reported are the virus particles found in some strains of Penicillium chrysogenum, P. funiculosum, P. stoloniferum, Aspergillus niger and A. Foetidus; cytoplasmic polyhedrosis virus; reovirus 3 virion and the replicative form of MS2 coliphage and of MU9 mutant coliphage.

However, the usefulness of double-stranded RNA is limited by its extremely short half life in human beings and in many farmyard animals and poultry. For example the duration of antiviral protection afforded by a single dose of double-stranded RNA, administered by subcutaneous injection in the pig is only one or two days. If double-stranded RNA is to be an economically viable protective agent for farmyard animals during an epidemic of viral infection, the duration of protection afforded by a single dose must be more than one or two days. The need for an antiviral agent having a longer duration of activity than double-stranded RNA alone is thus clear.

According to the present invention there is provided an antiviral substance which is a principally ionic complex in which the cations are organic polymer polycations which contain a repeat unit of formula (I):-

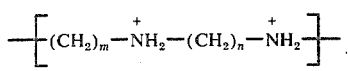

wherein $m$ and $n$ are the same or different and each is an integer from 3 to 5, and the anions are either (a) double-stranded ribonucleic acid polyanions, said double-stranded ribonucleic acid being of natural origin or (b) polyanions of a double-stranded derivative of a double-stranded ribonucleic acid of natural origin.

The term "double-stranded" used in connection with ribonucleic acid refers to the characteristic whereby two ribonucleic acid molecules are associated by hydrogen bonding between complementary bases in each molecule. Ribonucleic acids may vary in the degree of "double-strandedness."

The term "double-stranded ribonucleic acid of natural origin" means any double-stranded ribonucleic acid which is isolatable from a naturally-occurring source (e.g. those sources listed earlier in this specification), and excludes synthetic double-stranded ribonucleic acids such as Poly I : Poly C, Poly A : Poly U and Poly G : Poly C.

The term "double-stranded derivative of a double-stranded ribonucleic acid of natural origin" means any double-stranded ribonucleic acid of natural origin which has been subjected to a chemical or biochemical (e.g. enzymatic) reaction which alters the primary and/or secondary and/or tertiary structure (e.g. the N-oxides described in our British Patent Application No. 19448/70, British Pat. No. 1,284,150, or the alkali-modified double-stranded ribonucleic acids in our British Patent Application No. 1940/71, British Pat. No. 1,356,263), provided that the resultant derivative retains a substantial degree of base-pairing between complementary strands.

The double-strandedness of a double-stranded ribonucleic acid or a derivative of a double-stranded ribonucleic acid can be measured by two parameters known as the hyperchromicity and Tm. These parameters are obtained by recording the ultra violet absorption of the material at 258m$\mu$ while gradually raising the temperature of the material. The u.v. absorption value of a double-stranded material at this frequency increases with increasing temperature until a constant value is reached, corresponding to the absorption of the thermally denatured (i.e. single-stranded) ribonucleic acid. The difference between the two extremes of absorption expressed as a percentage of the absorption of the double-stranded material is termed the "hyperchromicity" of that material.

When the u.v. absorption at 258m$\mu$ of a double-stranded material is plotted against temperature, it is found that the absorption is greater than at low temperatures. The temperatures at which the absorption is mid-way between the absorption of the double-stranded material and that of the thermally denatured (i.e. single stranded) material is called the Tm of the material.

The cationic moiety present in the complexes of this invention is one which has a repeat unit of formula (I). The overall structure of one class of suitable cationic moieties can be represented by formula (II):-

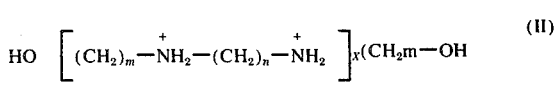

wherein $m$ and $n$ are as defined with respect to formula (I) and X is an integer or fractional number 4 which depends on the length of the polymer chain. Preferably X is in the range 4 to 3,000 and more preferably is in the range 5 to 500.

The polyanions present in the complex of this invention are (a) double-stranded ribonucleic acid polyanions, said double-stranded ribonucleic acid being of natural origin or (b) polyanions of a double-stranded derivative of a double-stranded ribonucleic acid of natural origin. Preferred sources of double-stranded ribonucleic acid include the virus like particles found in certain of the Penicillia, e.g. P. chrysogenum (British Pat. No. 1,170,929), P.stoloniferum (Banks et. al. Nature 218, 542 (1968)), P.cyaneofulyum (Banks et. al. Nature 223, 155 (1968)), and in certain of the Aspergilli eg., A.niger and A.foetidus (our co-pending British patent application No. 13826/70 British Pat. 1,300,259). Preferably also the component (a) or (b) should be capable of inducing interferon production in live mammals. (This can be confirmed by the method of Lampson et. al. G. P. Lampson, A. A. Tytell, A. K. Field, N. M. Nemes and Mr. Hillerman Proc. Nat. Acad. Scl., 58 (1967), 782).

The antiviral substance of this invention has been described as a principally ionic complex. The complex is characterized by a strong electrostatic interaction between the polymeric cationic moiety and the ribonucleic acid anionic moiety. However, other types of interaction may well operate. For example, it is believed that some form of "hydrophobic" bonding exists between the two components, although the precise nature of such bonding is not yet understood.

The preferred complexes of this invention are those in which all, or almost all, of the anionic sites on the double-stranded ribonucleic acid anions are neutralized by the ammonium sites in the polycation. Such complexes may be termed "1:1 complexes" or "highly neutralized complexes." Clearly the spacings between ammonium sites (i.e. the values of $m$ and $n$ in formulae (I) and (II)) will have an effect on the effectiveness of any particular polycation in complexing with RNA anion. Suitably the degree of charge neutralization is more than 60% preferably more than 75%.

The complexes of this invention may be prepared by a process which comprises contacting, in aqueous solution containing an elecrolyte, organic polymer polycations containing a repeating unit of formula (I) above, with either (a) double-stranded ribonucleic acid polyanions said double-stranded ribonucleic acid being of natural origin or (b) polyanions of a double-stranded derivative of a double-stranded ribonucleic acid of natural origin, and, if necessary, diluting the aqueous reaction mixture until the complex precipitates. If the molarity of the solution is not too high, after the contacting of the two components, the desired product precipitates out. If, however, the electrolyte concentration is very high, the complex may remain "in solution" (although strictly speaking in such high electrolyte concentrations the complex is probably dissociated) but it can be recovered as a precipitate on dilution. Preferably the contacting is carried out at high electrolyte concentrations and the complexes of this invention are precipitated on dilution.

The complexes of this invention are antiviral in activity, having a wide spectrum of activity against a variety of DNA and RNA viruses, e.g. encephalomyocarditis (EMC) virus, Semliki Forest virus, Foot and Mouth Disease virus and Herpes Simplex virus. It is believed that their mode of action is principally by induction of interferon in host cells, thereby conferring protection against virus attack. For this reason it is believed their primary utility lies in the prophylaxis of virus infection rather than in the treatment of established infections. The complexes are in general more resistant to ribonuclease degradation than the double-stranded ribonucleic acid itself.

Thus, in another of its aspects, the present invention provides a pharmaceutical composition comprising an antiviral complex as defined hereinbefore and one or more pharmaceutically acceptable carriers.

The choice of pharmaceutical carrier is determined by the preferred mode of administration and standard pharmaceutical practice. The mode of administration may be by injection, e.g. subcutaneously, intravenously or intramuscularly, in which case the carrier will be an injectable liquid in which the complex is suspended as a fine dispersion. In a few cases topical application of the complex is appropriate, e.g. in the eye or on mucous membrane. The composition of this invention may be administered alone or in combination with other agents used in the treatment of virus infections (e.g. vaccines) or for the relief of the symptoms of virus infections.

The following Examples are intended to illustrate the properties of, and methods of preparation of, some complexes of this invention, and also to illustrate in greater detail some of the features of the invention referred to earlier in this specification. In the following Examples, the abbreviation "d.s RNA" stands for "double-stranded ribonucleic acid."

EXAMPLE 1 a. Preparation of Polyamine Starting Material (4/5 polyamine)

1,4-Diaminobutane (20mM) was added to a stirred 50% aqueous solution of glutaraldehyde (20mM). Immediately a fibrous red precipitate was formed with the evolution of heat. The reaction vessel was cooled in an ice bath and the precipitate was broken down with a spatula. Tetrahydrofuran (10ml.) was added before adding the rest of the diaminobutane. After stirring for 0.5 hour, sodium borohydride (20mM) was added to the reaction mixture. The reduction, as shown by the evolution of hydrogen, proceeded slowly, the red precipitate turning pale yellow. As the precipitate was ground up with a spatula further reduction took place. The suspension and tetrahydrofuran washings (100ml.) were transferred to a round bottomed flask, left for 3 days at room temperature, then refluxed for 4 hours. The excess hydride was destroyed by adding water (1ml.). The tetrahydrofuran — soluble fraction was decanted, combined with one tetrahydrofuran washing and kept at $-20°$ C for two days, but no polymer crystallized out. The residue from the reaction was extracted with water, pH adjusted to 1.5 with dilute hydrochloric acid and then the aqueous extract was dialysed against distilled water (4 × 5 1) followed by freeze drying the product was a light brown powder (133mg.) and was given the internal test number PA/5A.

The tetrahydrofuran solution was concentrated down to give a thick oil (1.6g.). Part of this oil (1.38g.) was suspended in water and exactly neutralized with 5N hydrochloric acid (2.1ml.) to give a cloudy solution which was made clear by extraction with ether (30ml. × 3). The rest of the aqueous solution was dialyzed against water (1. lit × 1; 5. lit × 2, 3 days) and then freeze dried to give a light brown solid (586mg.) which was given the internal test number PA/5C.

On the basis of the n.m.r. spectrum, elemental analysis and gel filtration chromatography, both samples PA/5A and PA/5C were found to be similar. In the n.m.r. spectrum, there were two broad peaks at 8.2 and 6.9 (integral 5:4) which correspond to $-CH_2-CH_2-CH_2$ × 5 and $-CH_2-N^+H_2-$ × 4 as expected for the structure shown when X is large.

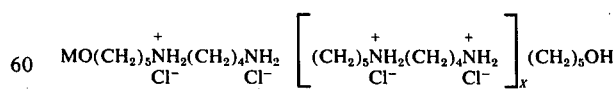

Gel filtration chromatography on bio-gel 1.5M indicated the presence of some high molecular weight polymer ($\chi > 50$) but that most of the material was of lower molecular weight ($\chi$ ca 10-15). In the elemental analysis, an excess of carbon was attributed to excess glutaraldehyde forming some cross-links.

Because of the length of the hydrocarbon sections, this polymer can be called a 4/5 polyamine.

b. Preparation of d.s RNA/Polyamine Complexes

4/5 Polyamine (PA/5A 28.2mg; PA/5C 183.5mg.) in 4M NaCl (4ml.) was added dropwise to a solution in 1.25M NaCl (30ml.) of d.s. RNA (500mg.) obtained from the virus particles found in *Penicillium chrysogenum* ATCC 10002 and the reaction mixture continuously stirred. The resulting clear 1.5M saline solution was left at room temperature overnight. Then distilled water (210ml.) was added dropwise very slowly. Initially the viscous solution contained many bubbles and it was difficult to see when precipitation started. However, when the solution was 1M saline, it had become much less viscous and a fine precipitate had formed. The rest of the water was then added more quickly (0.5 hr). The precipitate was centrifuged down from the suspension combined with 0.15M saline washing (20ml.) and the supernatant decanted. The spernatant contained 1.4% of the RNA but, after filtration, only 2mg. (0.3%) of the RNA remained in solution and this RNA was not fully double stranded in character. The precipitate was resuspended in 0.15M saline at a concentration of 20mg/ml. (measured by u.v. spectrum of an aliquot dissolved in 1.5M saline). This suspension was given the internal test no. INT 1010.

EXAMPLE 2 a. Polyamine starting materials (5/5 polyamine)

1,5 Diaminopentane (30mM) was added dropwise to a solution of glutaraldehyde (40mM) in dry tetrahydrofuran (10ml.). A sticky precipitate was formed. After 0.5 hour sodium borohydride (40mM) in tetrahydrofuran (10ml.) was added. The product was worked up as for PA/5A and PA/5C in Example 1 to give two samples designated E13/B (0.23g.) and E13/A (0.46g.) respectively. On the basis of n.m.r. spectra, these samples were assigned the structure:-

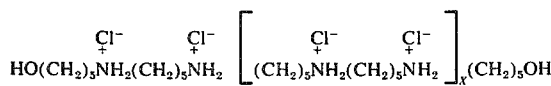

The value of X was estimated to be greater than 10. An excess of carbon in the elemental analysis was attributed to excess glutaraldehyde. This complex is a 5/5 polyamine.

b. d.s. RNA/polyamine complex

Using 50mg. of sample E/13A (5/5 polyamine) the procedure described in Example 1(b) was repeated to produce internal test sample INT 973.

EXAMPLE 3 a. Polyamine starting material (4/5 polyamine)

Glutaraldehyde (25.03g. freshly distilled, ca 100% free aldehyde as indicated by nmr.) and diaminobutane (22.0g., 25.1ml.) were slowly added simultaneously to water (300ml.) which was mechanically stirred and kept near 0° C with an ice/salt bath. Immediately a thick white precipitate was formed. After 45 min., freshly distilled THF (500ml.) was added and the precipitate slowly dissolved. Sodium borohydride (10g.) was added slowly and then the reaction was left stirring overnight at room temperature. A further portion of sodium borohydride (1g) was added to ensure complete reduction. Then the solution was made weakly acidic (pH 6) with dilute hydrochloric acid in order to destroy the excess hydride and to form the salt of the polybase. The THF was evaporated off and the resulting solution, after filtration, was extensively dialyzed vs deionized water followed by freeze drying to give an off-white solid (PA 7, 9.35g.). In a repeat preparation, a white solid (PA 8, 5.1g.) was obtained. N.M.R. and analysis indicate that these materials are similar to the polybase of Example 1.

b. d.s. RNA/polyamine complex

Two batches of complex were prepared by the same method as described in Example 1(b). In the first batch ds-RNA (500mg.) was complexed with 4/5 polyamine chloride (PA 7, 167mg.) and in the second batch ds-RNA (6g.) was complexed with 4/5 polyamine chloride (PA 8, 2g.). Both preparations gave the products as a very fine white suspension in 0.1M saline.

The former complex (from PA 7) was given the internal test No. INT 2004; and that from PA 8 was given test no. 2005.

BIOLOGICAL DATA

1. Data for complexes of Examples 1 and 2

Isotonic saline solutions of complexes INT 973 (Example 2) and INT 1010 (Example 1) were sent for biological evaluation. They were compared with the parent uncomplexed d.s. RNA in mice. The route of administration was by intraperitoneal injection and the test virus was encephalomyocarditis virus (EMC). Compounds were administered in the highest dose believed to be relatively nontoxic and at one tenth of that dose. The results are shown in Table I:

TABLE I

| | | NUMBER DEAD DIVIDED BY TOTAL NUMBER IN GROUP | | | | | |
|---|---|---|---|---|---|---|---|
| | | ANTIVIRAL DATA | | | | | |
| | | Administered 3 days prior to infection | Administered 1 day prior to infection | TOXICITY | | | |
| TEST COMPOUND | Compound dose mg/kg. | ¹VIRUS DOSE⁻⁴ | | COMPOUND DOSE mg/kg | | | $LD_{50}$ (mg/kg) |
| | | | | 100 | 50 | 25 | |
| d.s. RNA | 5 | 3/10 | | | | | |
| | 0.5 | 9/10 | 1/10 | 10/10 | 10/10 | 9/10 | <25 |
| 973 | 10 | 4/10 | 4/10 | 7/10 | 5/10 | 2/10 | 60 |
| | 1 | 4/9 | 5/10 | | | | |
| 1010 | 100 | 2/9 | 3/10 | 0/10 | 0/10 | 0/10 | >>100 |

TABLE I-continued

| | | NUMBER DEAD DIVIDED BY TOTAL NUMBER IN GROUP | | | | | |
|---|---|---|---|---|---|---|---|
| | | ANTIVIRAL DATA | | | | | |
| | | Administered 3 days prior to infection | Administered 1 day prior to infection | TOXICITY | | | |
| TEST COMPOUND | Compound dose mg/kg. | ¹VIRUS DOSE⁻⁴ | | COMPOUND DOSE mg/kg | | | $LD_{50}$ (mg/kg) |
| | | | | 100 | 50 | 25 | |
| | 10 | 5/10 | 6/10 | | | | |

¹$10^{-4}$ dilution of virus stock, ca 10 $LD_{50}$ virus challenge.

From the above it can be seen that the complexes of this invention are less toxic than uncomplexed d.s. RNA and thus can be given in higher doses. The antiviral data shows that whereas d.s. RNA is significantly less active when given 3 days prior to infection, both INT 973 and 1010 are about equally active at 3 days and 1 day prior to infection. In a separate series of experiments using INT 1010 only, these results were confirmed and the same tendency was observed when the mice were dosed by the subcutaneous route:-

TABLE II

| | | ANTIVIRAL DATA (EMC) NO. DEAD OUT OF 10 IN EACH GROUP | | | |
|---|---|---|---|---|---|
| | | Administered i.p. (s.c.) 7 days prior to infection | | Administered i.p. (s.c.) 1 day prior to infection | |
| INT. NO. | COMPOUND DOSE | VIRUS DOSE $10^{-3}$ | VIRUS DOSE $10^{-4}$ | VIRUS DOSE $10^{-3}$ | VIRUS DOSE $10^{-3}$ |
| 1010 | 200 | 7 | 2 (7) | 7 | 1 (9) |
| | 20 | 9 | 5 (10) | 8 | 1 (10) |
| d.s. RNA | 10 | 10 | 7 (10) | 1 | 2 (3) |
| | 1 | 10 | 9 (9) | 9 | 3 (8) |

The mortality in undosed controls was 19/20 at a virus challenge of $10^{-3}$ and 20/20 (20/20) at a virus challenge of $10^{-4}$.

2. Data for 4/5 polyamine complexes of Example 3
  a. The acute toxicity of each of the complexes INT 2004 and INT 2005 was determined by the intraperitoneal route and compared with date for the uncomplexed d.s.
  RNA. The results are shown in Table III; and demonstrates the remarkably low toxicity of the complex INT 2005 prepared from the polyamine batch PA 8.

TABLE III

| INT. NO. | VEHICLE | Deaths (group size = 10) (mg/kg) | | | | $LD_{50}$ (mg/kg.) (graphical) |
|---|---|---|---|---|---|---|
| | | 25 | 50 | 100 | 500 | |
| d.s. RNA | PBS | 3 | 10 | 10 | — | 29 |
| | oil* | 1 | 6 | 10 | — | 44 |
| 2004 | 0.15 M NaCl | — | — | 0 | 7 | 360 |
| 2005 | 0.15 M NaCl | — | — | 0 | 0 | > 500 |

* Incomplete freund's adjuvant.

b. Duration of Activity

The duration of the protection offered by INT 2005 against low and high challenge levels of EMC virus (8 and 80 $LD_{50}$) was evaluated at discrete time intervals up to 5 weeks. The time intervals, dose-rates and routes are shown in Tables IV and V. (i.p. = intraperitoneal; s.c. = subcutaneous). Duration of Protection of Ds-RNA Complexes

TABLE IV

| | | | 8 × $LD_{50}$ Pretreatment Time (Days) | | | |
|---|---|---|---|---|---|---|
| Drug | Dose mg/kg | Route | 1 | 7 | 21 | 35 |
| | | | (Deaths/Group Size) | | | |
| d. s. RNA | 5 | i.p. | 0/10 | 3/10 | — | — |
| d.s. RNA | 5 | s.c. | 0/10 | 7/10 | — | — |
| INT. 2005 | 500 | i.p. | 0/10 | 0/10 | — | 0/10 |
| INT. 2005 | 500 | s.c. | 2/10 | 4/10 | 7/10 | 0/10 |
| Control | | | 10/10 | | | |

TABLE V

| | | | 80 × $LD_{50}$ Pretreatment Time (Days) | | | |
|---|---|---|---|---|---|---|
| Drug | Dose mg/kg | Route | 1 | 7 | 21 | 35 |
| | | | (Deaths/Group Size) | | | |
| d.s. RNA | 5 | i.p. | 0/10 | 10/10 | — | — |
| d.s. RNA | 5 | s.c. | 2/10 | 10/10 | — | — |
| INT. 2005 | 500 | i.p. | 0/10 | 0/10 | — | 1/10 |
| INT. 2005 | 500 | s.c. | 9/10 | 8/10 | 7/10 | 9/10 |
| Control | | | 10/10 | | | |

I claim:

1. A pharmaceutical composition useful for treating susceptible DNA and RNA viral infections which comprises an antiviral amount of an antiviral substance which is a principally ionic complex in which the cations are organic polymer polycations which contains a repeat unit of formula (I):

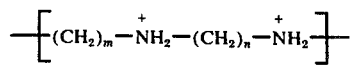

wherein $m$ and $n$ are the same or different and each is an integer from 3 to 5 and the anions are either (a) double-stranded ribonucleic acid polyanions, said double-stranded ribonucleic acid being of natural origin or (b) polyanions of a double-stranded N-oxide or alkali modified derivative of a double-stranded ribonucleic acid of natural origin, in combination with a pharmaceutically acceptable non-toxic diluent or carrier.

2. A pharmaceutical composition according to claim 1 wherein the organic polymer polycations have formula (II):

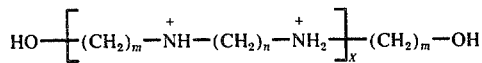

wherein $m$ and $n$ are the same or different and each is an integer from 3 to 5 and X is an integer or fractional number from 4 to 3,000.

3. A pharmaceutical composition according to claim 2 wherein X is from 5 to 500.

4. A pharmaceutical composition according to claim 1 wherein the double-stranded ribonucleic acid component is derived from the virus particles found in infected strains of Penicillium chrysogenum, Penicillium stoloniforum, Penicillium cyaneofulvum, Aspergillus niger, or Aspergillus foetidus.

5. A pharmaceutical composition according to claim 1 wherein more than 60% of the anionic sites on the double-stranded ribonucleic acid anions are neutralized by the ammonium sites in the polycation.

6. A pharmaceutical composition according to claim 5 wherein more than 75% of the anionic sites on the double-stranded ribonucleic acid anions are neutralized by the ammonium sites in the polycation.

7. A pharmaceutical composition according to claim 1 in parenteral administration form.

8. A pharmaceutical composition according to claim 1 in topical application form.

* * * * *